(12) United States Patent
Hebecker et al.

(10) Patent No.: US 6,771,734 B2
(45) Date of Patent: Aug. 3, 2004

(54) METHOD AND APPARATUS FOR GENERATING A VOLUME DATASET REPRESENTING A SUBJECT

(75) Inventors: Axel Hebecker, Spardof (DE); Joachim Hey, Bornheim (DE); Matthias Mitschke, Nuremberg (DE); Lutz-Peter Nolte, Huenibach (CH); Oliver Schuetz, Erlangen (DE); Heinz Waelti, Thun (CH)

(73) Assignees: Siemens Aktiengesellschaft, Münich (DE); Medivision AG, Oberdorf/BL (CH)

( * ) Notice: Subject to any disclaimer, the term of this patent is extended or adjusted under 35 U.S.C. 154(b) by 0 days.

(21) Appl. No.: 10/366,048

(22) Filed: Feb. 13, 2003

(65) Prior Publication Data

US 2003/0152195 A1 Aug. 14, 2003

(30) Foreign Application Priority Data

Feb. 14, 2002 (DE) .......................................... 102 06 190

(51) Int. Cl.[7] ................................................ A61B 6/03
(52) U.S. Cl. .............................. 378/8; 378/95; 378/901
(58) Field of Search .............................. 378/8, 4, 901, 378/95, 205, 207; 382/132

(56) References Cited

U.S. PATENT DOCUMENTS

| | | | | |
|---|---|---|---|---|
| 5,287,276 A | * | 2/1994 | Crawford et al. | ............... 378/4 |
| 5,764,721 A | * | 6/1998 | Light et al. | ..................... 378/4 |
| 6,198,837 B1 | * | 3/2001 | Sasano et al. | .............. 382/132 |
| 6,289,235 B1 | * | 9/2001 | Webber et al. | .............. 600/426 |
| 6,430,432 B1 | * | 8/2002 | Wilting et al. | .............. 600/425 |
| 6,491,429 B1 | * | 12/2002 | Suhm | ......................... 378/205 |
| 2001/0053204 A1 | * | 12/2001 | Navab et al. | ............... 378/205 |

* cited by examiner

*Primary Examiner*—David V. Bruce
*Assistant Examiner*—Irakli Kiknadze
(74) *Attorney, Agent, or Firm*—Schiff Hardin LLP

(57) ABSTRACT

In a method and an apparatus for generating a volume dataset of a subject taking a movement of the subject into consideration, a referencing base is arranged at the subject, so that the positions and the orientations of the referencing base can be acquired during a registration of a series of 2D projections of the subject. The volume dataset of the subject is generated on the basis of the series of 2D projections as well as based on the deviations of the positions and of the orientations of the referencing base from a fixed reference position of the referencing base that are determined for all 2D projections of the series.

10 Claims, 1 Drawing Sheet

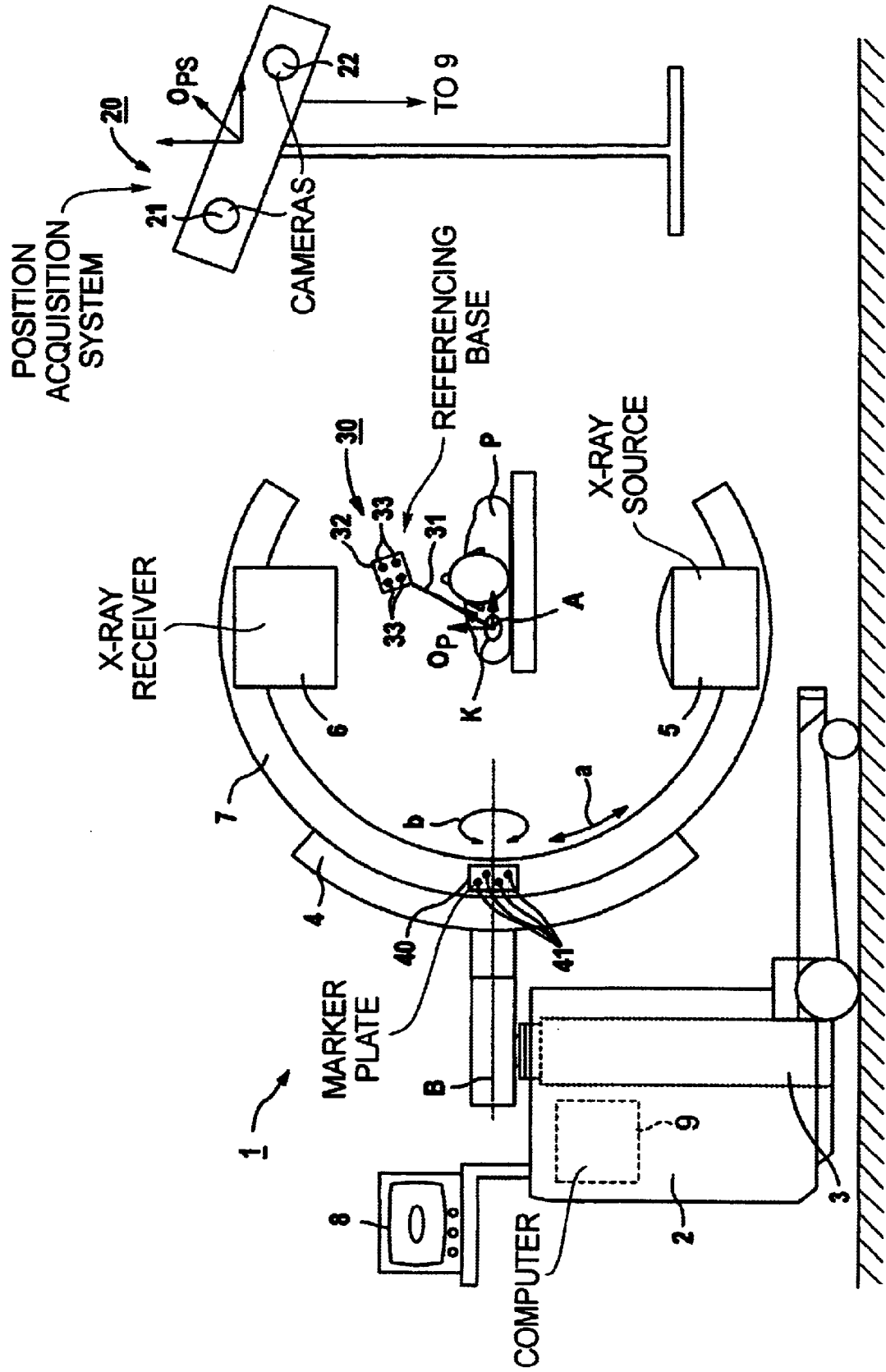

METHOD AND APPARATUS FOR GENERATING A VOLUME DATASET REPRESENTING A SUBJECT

BACKGROUND OF THE INVENTION

1. Field of the Invention

The present invention is directed to a method and to an apparatus for generating a volume dataset of a subject with a C-arm X-ray apparatus while taking a movement of the subject during a registration of a series of 2D projections of the subject into consideration.

2. Description of the Prior Art

For generating a volume dataset of a subject, a C-arm of a C-arm X-ray apparatus is rotated through approximately 190° around the subject in a time span of several seconds, with the 2D projections of the series being registered from different projection directions of the subject. The volume dataset of the subject can be generated from the 2D projections using projection matrices in a reconstruction algorithm.

Published United States Application 2001/0053204 discloses a calibration method for a C-arm X-ray apparatus, wherein projection geometries of the C-arm X-ray apparatus that are stored in projection matrices are determined with the assistance of a position acquisition system in order to be able to reconstruct a volume dataset of the subject in a subject measurement from a series of 2D projections acquired from different projection directions.

U.S. Pat. No. 6,289,235 discloses a method wherein markers are arranged in a fixed position relative to a subject. 2D projections of the subject and the markers are acquired from different projection directions with a radiation source and a reception device. Projection geometries for the reconstruction of a 3D image of the subject can be derived from the markers imaged in the 2D projections.

Movements on the part of the subject to be imaged, for example respiratory movements of a patient, during the registration of the 2D projections are problematical for the generation of the volume dataset. These respiration-produced movements of a patient are not compensated by the reconstruction algorithm. Movements of a subject during the registration of a series of 2D projections accordingly lead to a qualitatively poorer result of the reconstruction, i.e. to a qualitatively poorer volume dataset of the subject. In medical applications, the volume dataset generated from a patient even can be diagnostically useless.

In order to counteract respiration-produced reconstruction artifacts, images of patients are registered with ECG-triggering. ECG-triggering, however, has the disadvantage that additional apparatus are required for generating a volume dataset, which can be an impediment particularly for intra-operative employment.

German OS 41 37 652 discloses a method wherein an X-ray CT, scanner acquires projection data from a series of views during the scanning of a rib cage of a patient. Movements of the rib cage of the patient due to respiration during the scanning are thereby also acquired. The motion data are employed together with a geometrical model of the rib cage movement in order to calculate factors that correct the acquired projection data and reduce motion artifacts in an image.

SUMMARY OF THE INVENTION

An object of the present invention is to provide a method and an apparatus of the type described above wherein the generation of a volume dataset of a moving subject is simplified.

This object is inventively achieved in a method and an apparatus for generating a volume dataset of a moving subject, wherein a referencing base is arranged at the subject in a defined way, and the position and the orientation of the referencing base are acquired by a position acquisition system. During the exposure of the series of 2D projections of the subject, the position and the orientation of the referencing base is determined with the position acquisition system and the position of the C-arm is determined substantially simultaneously with at least one exposure of a 2D projection of the series of 2D projections. Moreover, the deviation of the current position and of the current orientation of the referencing base from a previously defined reference position of the referencing base is determined for the 2D projection. Via the referencing base arranged at the subject in a defined way, accordingly, the deviations of the current position and of the current orientation of the subject from its reference position, corresponding with the reference position of the referencing base can be determined. Since the deviation of the referencing base or the deviation of the subject from its reference position has been determined for a 2D projection and the position of the C-arm for the 2D projection also has been determined, these can be taken into consideration in the generation of the volume dataset, so that a qualitatively higher-grade volume dataset can be generated.

In a version of the invention, the imaging of the subject in the 2D projection is shifted—before the generation of the volume dataset—on the identified deviation of the referencing base allocated to this 2D projection or, the deviation of the subject from its reference position, and the position of the C-arm allocated to the 2D projection, for taking a movement of the subject in at least one 2D projection of the series of 2D projections into consideration. In this way, a 2D projection is generated with an imaging of the subject shifted according to the deviation of the position and the orientation of the subject from its reference position, and thus the object movement is compensated. A translational shift of the imaging of the subject parallel to the image plane of the 2D projection preferably ensues, particularly since subject movements perpendicular to the image plane of the 2D projection have only a minimal influence on the 2D projection and the reconstruction result. As a rule, the imaging of the subject is shifted in all 2D projections of the series of 2D projections corresponding to its deviation from its reference positions, and the reconstruction algorithm for generating the volume dataset is implemented only subsequent thereto. Because practically all movements of the subject during the exposure of the series of 2D projections are taken into consideration by the corresponding shifts of the images of the subject in the 2D projections, a qualitatively higher-grade volume dataset of the subject is obtained.

In another embodiment of the invention each projection matrix is modified—before the generation of the volume dataset—based on the deviation of the identified referencing base allocated to its 2D projection, or on the basis of the identified deviation of the subject from its reference position, and the position of the C-arm allocated to this 2D projection for taking a movement of the subject into consideration for at least one 2D projection of the series of 2D projections. In a second version of this embodiment, at least one extrinsic imaging parameter of the projection matrix is modified. Whereas the movements of the object during the exposure of the 2D projections in the above-described version are compensated by shifts of the images of the subject in the 2D projections, the second version of the invention is based on the consideration of viewing the subject as a system at rest and viewing the X-ray system as a moving system. In the case of the second version, accordingly, the extrinsic imaging parameters of the projection matrices are modified according to the movements of the subject since the extrinsic imaging parameters describe the position and orientation of the X-ray system, for example the focus of the X-ray source. By suitable modification of the extrinsic imaging parameters of the projection matrices, accordingly, movements of the subject during the exposure of the series of 2D projections can likewise be taken into consideration. When generating the volume dataset of the subject, only the modified projection matrices are employed by the reconstruction algorithm, so that a higher-quality volume dataset again is achieved.

In another embodiment of the invention the reference position of the referencing base, which corresponds with the reference position of the subject, is fixed with the exposure of the first 2D projection of the series of 2D projections.

DESCRIPTION OF THE DRAWINGS

An exemplary embodiment of the invention is shown in the schematic figure, which illustrates the employment of the inventive apparatus for the generation of a volume dataset of a bone of a patient.

DESCRIPTION OF THE PREFERRED EMBODIMENTS

The apparatus has a known C-arm X-ray apparatus 1 having an apparatus cart 2 with a lifting mechanism 3 to which a support 4 is connected. A C-arm 7 that is provided with an X-ray source 5 and an X-ray receiver 6 and that is isocentrically adjustable around the orbital axis A along its circumference (see double arrow 'a') in the present exemplary embodiment is seated at the support 4. The C-arm 7 also is isocentrically pivotable in the directions of the double arrow 'b' around its angulation axis B together with the support 4.

2D projections of body regions of the patient P or a volume dataset of a body region of the patient P can be acquired in a known way with the C-arm X-ray apparatus 1. In the present exemplary embodiment, a volume dataset of the bone K of the patient P is to be generated in a computer 9 from the 2D projections, using projection matrices. In the exemplary embodiment, respiration-produced movements of the bone K in the registration of the series of 2D projections prove problematical in the generation of the volume dataset. These respiration-produced movements of the bone K are not compensated by the reconstruction algorithm for generating the volume dataset, so that a qualitatively poorer volume dataset of the bone would be reconstructed.

In order to counteract this, an optical position acquisition system 20 is provided in the exemplary embodiment, having two cameras 21, 22. The position and the orientation of a referencing base 30 firmly attached to the bone K of the patient P can be determined in a coordinate system OPS of the position acquisition system 20 using the position acquisition system 20. In the exemplary embodiment, the referencing base 30 is a rod 31 formed of an X-ray-transparent material that is secured to the bone K of the patient in a way that is not shown. To this end, the bone K of patient p has been provided with a hole into which the one end of the rod 31 has been introduced. An X-ray-transparent marker plate 32 that is provided with X-ray-transparent markers 33 that can be acquired by the position acquisition system 20 is arranged at the rod 31 at the end thereof that is remote from the patient P.

A marker plate 40 having markers 41 that can be acquired by the position acquisition system is arranged in a defined way at the C-arm 7 of the C-arm X-ray apparatus 1. A relationship between the coordinate system OPS allocated to the position acquisition system and a patient coordinate system OP can be produced in this way.

For acquiring a volume dataset of the bone K of the patient P, the C-arm 7 is brought into a specific initial position and is preferably equidistantly displaced either around its orbital axis A or around its angulation axis B in an angular range of approximately 190°, whereby approximately 50 to 100 2D projections of the bone are acquired from different projection directions. In order to be able to take the respiration-produced movements of the bone K into consideration, the position and the orientation of the referencing base 30 in the coordinate system OPS is determined by the position acquisition system 20 in the exemplary embodiment substantially simultaneously with the exposure of each 2D projection. The determination of the positions and of the orientations of the referencing base 30 ensues by evaluation of the camera images of the markers 33 of the referencing base 30 registered by the cameras 21, 22. To this end, the computer 9 (for another component) of the C-arm X-ray apparatus 1 and the position acquisition system 20 are electrically connected to one another schematically indicated, so that a trigger pulse for the exposure of a 2D projection also substantially simultaneously effects the registration of camera images of the referencing base 30 with the cameras 21, 22.

The marker plate 40 attached to the C-arm 7 in a defined way also is imaged in the camera images of the cameras 21, 22 registered in this way, so that the position and the orientation of the C-arm 7 of the C-arm X-ray apparatus 1 in the coordinate system OPS of the position acquisition system also can be determined on the basis of the markers 41 of the marker plate 40. It can suffice to determine the position and the orientation of the C-arm 7 with reference to the coordinate system OPS with the position acquisition system 20 before the exposure of the 2D projections. The other position information can be taken from known position sensors (not shown) of the C-arm X-ray apparatus 1 for the position of the C-arm 7, or the position particulars are derived from the initial position of the C-arm 7 taking the equidistant adjustment of the C-arm 7 during the registration of the series of 2D projections into consideration. The position information determined by the position acquisition system 20 as well as the outputs of the position sensors (if present) are supplied to the computer 9. Moreover, the position details can be derived from the projection matrices.

In the exemplary embodiment, the reference position of the referencing base 30 is defined with the position acquisition system 20 with respect to the coordinate system OPS upon exposure of the first 2D projection of the series of 2D projections. The position and the orientation that the referencing base 30 exhibits in the exposure of this 2D projection relative to the coordinate system OPS represents the reference position to which the positions and orientations of the referencing base 30 identified upon exposure of the further 2D projections of the series of 2D projections are compared. During the course of the inventive method, the deviation of the current position and the current orientation of the referencing base 30 from the reference position of the referencing base 30 are ultimately determined for each 2D projection of the series of 2D projections. Because the referencing base 30 is allocated to the bone K in a defined way, the deviation of the current position and the current orientation of the bone K from the reference position derived from the first 2D projection in the series of 2D projections also can be determined.

As already mentioned, a relationship between the patient coordinate system OP and the coordinate system OPS of the position acquisition system 20 can ultimately be produced due to the determination of the position and of the orientation of the C-arm in the coordinate system OPS of the position acquisition system 20. Accordingly, the deviations of the bone K identified relative to the coordinate system OPS of the position acquisition system 20 also can be identified or included in the patient coordinate system OP that is relevant for the 2D projections.

In a first version of the invention, the imaging of the bone K in a 2D projection of the series of 2D projections can be shifted based on the identified deviation of the bone K from its reference position that is allocated to this 2D projection that the respiration-produced movement of the bone K relative to this reference position is compensated in the 2D projection. This compensation is implemented in the computer 9 for all 2D projections, and no shift of the imaging of the bone K at all is required in some 2D projections under certain circumstances. This is always the case when the bone was in its reference position during the exposure of the 2D projection. Insofar as necessary, a translational shift of the image of the bone parallel to the imager plane of the 2D projection preferably ensues.

The generation of the volume dataset of the bone K ultimately ensues in the computer 9 on the basis of the 2D projections modified using the known projections matrices, previously determined in a known way, and using the reconstruction algorithm. In this way, a qualitatively high-grade volume dataset of the bone K is obtained wherein the respiration-conditioned movements of the bone K during the registration of the series of 2D projections are compensated. In a known way, 2D images or 3D images of the bone of the patient P then can be generated from the volume dataset and can be presented on a viewing device 8.

The determination of the deviations, the shift of the images of the bone K in the 2D projections, as well as the implementation of the reconstruction algorithm preferably ensues by means of an image computer of the C-arm X-ray apparatus 1 that is not explicitly shown, that is known.

In a second version of the invention, the deviations of the bone K from its reference position that can be determined with reference to the patient coordinate system OP can be employed for modifying the projection matrices of the C-arm X-ray apparatus 1. This approach is based on viewing the bone K as a system that is at rest and viewing the X-ray system as a moving system. The extrinsic imaging parameters of the projection matrices are varied in the computer 9, these indicating the position and the orientation of the X-ray system relative to the patient coordinate system OP. Based on the identified deviation of the bone K from its reference position, accordingly, the projection matrix allocated to this 2D projection is modified by modifying at least one extrinsic imaging parameter of the projection matrix corresponding to the deviation. As already mentioned in the first version, a modification of the projection matrices by the image computer also ensues in the second version only when a deviation of the bone K from its reference position is present in a 2D projection. Accordingly, the reconstruction algorithm is implemented by the image computer of the C-arm X-ray apparatus 1 with the originally registered 2D projections and the modified projection matrices.

An optical position acquisition system 20 is employed above in the exemplary embodiment, however, the position acquisition system need not necessarily be an optical acquisition system. An electromagnetic position acquisition system or a position acquisition system based on acoustic waves can alternatively be employed. If so, the optical markers 33 or 41 are replaced by electromagnetic transmitters or acoustic transmitters, and the cameras 21, 22 are to be replaced by suitable receivers for electromagnetic waves or receivers for acoustic waves. As another alternative, a mechanical system can also be employed for the position acquisition.

Moreover, some other, suitable referencing base can also be employed for the implementation of the inventive method instead of the described referencing base.

The referencing base need not necessarily be secured to a bone of the patient, as described above. It suffices to attach the referencing base to the patient such that it does not become dislocated relative to the patient during the measurement.

The invention is explained above for a medical application, but is not limited to the medical field.

We claim as our invention:

1. A method for generating a volume dataset representing at least a portion of a subject experiencing movement comprising the steps of:

disposing a referencing base at a subject experiencing movement, and continually identifying a position and an orientation of said referencing base with a position acquisition system;

obtaining a series of 2D projections of at least a portion of said subject with a C-arm X-ray system having a C-arm, and determining a position of said C-arm with said position acquisition system substantially simultaneously with at least one exposure of a 2D projection of the series of said 2D projections;

in a computer, determining a deviation of a current position and a current orientation of said referencing base from a reference position for said reference base for said at least one 2D projection; and generating a volume dataset from said series of 2D projections using projection matrices, by generating said volume dataset dependent on said deviation of said reference base associated with said at least one 2D projection and said position of said C-arm obtained substantially simultaneously with said at one 2D projection.

2. A method as claimed in claim 1 wherein said volume dataset is generated dependent on said deviation by, prior to generating said volume dataset, shifting an image of said subject in said at least one 2D projection dependent on said deviation of said reference base associated with said at least one 2D projection.

3. A method as claimed in claim 1 wherein said volume dataset is generated dependent on said deviation by, prior to generating said volume dataset, modifying a projection matrix associated with said at least one 2D projection dependent on said deviation of said referencing base for said at least one 2D projection and dependent on said position of said C-arm obtained substantially simultaneously with said at least one 2D projection.

4. A method as claimed in claim 3 wherein said projection matrix allocated to said at least one 2D projection comprises extrinsic imaging parameters, and wherein the step of modifying said projection matrix comprises modifying at least one of said extrinsic imaging parameters.

5. A method as claimed in claim 1 wherein said series of 2D projections includes a first 2D projection, and comprising the step of fixing said reference position of said referencing base using said first 2D projection.

6. An apparatus for generating a volume dataset representing at least a portion of a subject experiencing movement comprising:

a referencing base at a subject experiencing movement;

a C-arm X-ray system having a C-arm for obtaining a series of 2D projections of at least a portion of said subject;

a position acquisition system for continually identifying a position and an orientation of said referencing base and for determining a position of said C-arm with said position acquisition system substantially simultaneously with at least one of said 2D projections;

a computer in communication with said position acquisition system for determining a deviation of a current position and a current orientation of said referencing base from a reference position for said reference base for said at least one 2D projection; and said computer generating a volume dataset from said series of 2D projections using projection matrices, by generating said volume dataset dependent on said deviation of said reference base associated with said at least one 2D projection and said position of said C-arm obtained substantially simultaneously with said at one 2D projection.

7. An apparatus for generating a volume dataset as claimed in claim 6 wherein said computer generates said volume dataset dependent on said deviation by, prior to generating said volume dataset, shifting an image of said subject in said at least one 2D projection dependent on said deviation of said reference base associated with said at least one 2D projection.

8. An apparatus for generating a volume dataset as claimed in claim 6 wherein said computer generates said volume dataset dependent on said deviation by, prior to generating said volume dataset, modifying a projection matrix associated with said at least one 2D projection dependent on said deviation of said referencing base for said at least one 2D projection and dependent on said position of said C-arm obtained substantially simultaneously with said at least one 2D projection.

9. An apparatus for generating a volume dataset as claimed in claim 8 wherein said projection matrix allocated to said at least one 2D projection comprises extrinsic imaging parameters, and wherein computer modifies said projection matrix comprises by at least one of said extrinsic imaging parameters.

10. An apparatus for generating a volume dataset as claimed in claim 6 wherein said series of 2D projections includes a first 2D projection, and wherein said computer fixes said reference position of said referencing base using said first 2D projection.

* * * * *